United States Patent [19]

Williams

[11] Patent Number: 4,544,357

[45] Date of Patent: Oct. 1, 1985

[54] THROAT GUARD APPARATUS

[76] Inventor: Aaron T. Williams, 4023 SE. 19th Pl., #107, Cape Coral, Fla. 33904

[21] Appl. No.: 514,031

[22] Filed: Jul. 15, 1983

[51] Int. Cl.⁴ ............................................... A61C 5/14
[52] U.S. Cl. .................................................... 433/136
[58] Field of Search ............... 433/136, 137, 138, 140; 128/12

[56] References Cited

U.S. PATENT DOCUMENTS

| | | | |
|---|---|---|---|
| 590,460 | 9/1897 | Mehlig | 128/20 |
| 1,401,646 | 12/1921 | Ronn | 433/93 |
| 1,774,285 | 8/1930 | Middaugh | 433/137 |
| 3,406,452 | 10/1968 | McConville | 433/137 |
| 3,662,466 | 5/1972 | McConville | 260/397.45 |
| 3,772,790 | 11/1973 | Swan-Gett et al. | 433/136 |
| 4,259,067 | 3/1981 | Nelson | 433/93 |

OTHER PUBLICATIONS

Oral Surgery, Medicine, Pathology, 48(3) Sep. 1979, "Accidental Swallowing of an Endontic Instrument", by C. P. Govila, B.D.S. (Luck), M.D.S. (Bom.).
Oral Surgery, Medicine, Pathology, 24(5) Nov. 1967, "Accidental Swallowing of an Endontic Instrument", by Arden G. Christen, Major USAF (DC).
Am. Dent., 37(4) Winter 1978, "Accidental Swallowing of a Pin Wrench", by Wayne W. Barkmeier, D.D.S., M.S., Herbert Abrams, B.A., D.D.S., M.S. and Peter S. Barringer, B.A., D.M.D.
JADA, vol. 97, Sep. 1978-"Prevention of Swallowing or Aspiration of Foreign Objects", by Wayne W. Barkmeier, DDS., MS, Robert L. Cooley, DMD, MS and Herbert Abrams, DDS, MS.
The Journal of Prosthetic Dentistry, vol. 46, No. 6, Dec. 1981, "A Method to Prevent Swallowing or Aspiration of Cast Restorations", by Richard Jacobi, D.D.S., and Herbert T. Shillingburg, Jr., D.D.S.
General Denistry/Jan.-Feb. 1978, "Displaced Post and Core in the Epiglottic Vallecula", by Andrew S. Scott, D.D.S., and Benjamin E. Dooley, B.S., M.S., D.M.D., P.I.C.D.
Oral Surg., Oct., 1971, "Accidental Swallowing of an Endontic Instrument", by Jose Goultschin, D.D.S. and Barbara Heling, M.D.

Primary Examiner—Robert Peshock
Attorney, Agent, or Firm—Cushman, Darby & Cushman

[57] ABSTRACT

A disposable throat guard and a device for resiliently maintaining it therewith for use as a combined throat guard system includes a first pair of wire members of generally U-shaped configuration for resiliently engaging a flexible air permeable sheet material, an oversized portion which is held in place by the first pair of wire members over a patient's lower arch, a third wire member of generally U-shaped configuration with its ends resiliently connected adjacent ends of the first two wire members and biased to an opened bi-valve position so that when the device is placed in the mouth of the patient (between the teeth and cheeks), it functions to maintain the first two wire members (and the therein retained throat guard) in place in the patient's mouth. The throat guard of flexible sheet material has a rear leaf portion which, when folded upwardly and forwardly will substantially obstruct the passage between the mouth cavity and throat of the patient.

13 Claims, 5 Drawing Figures

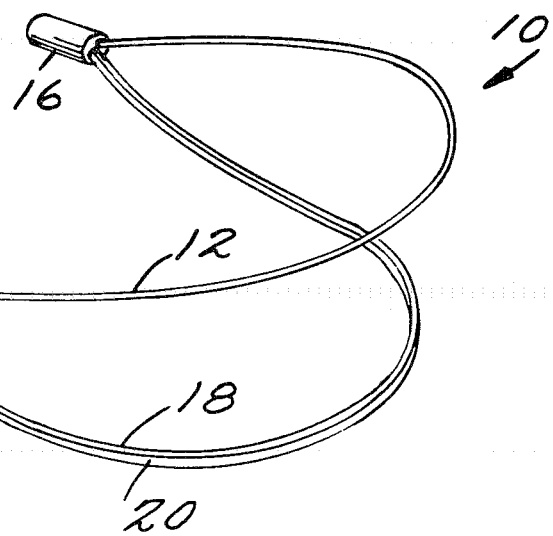
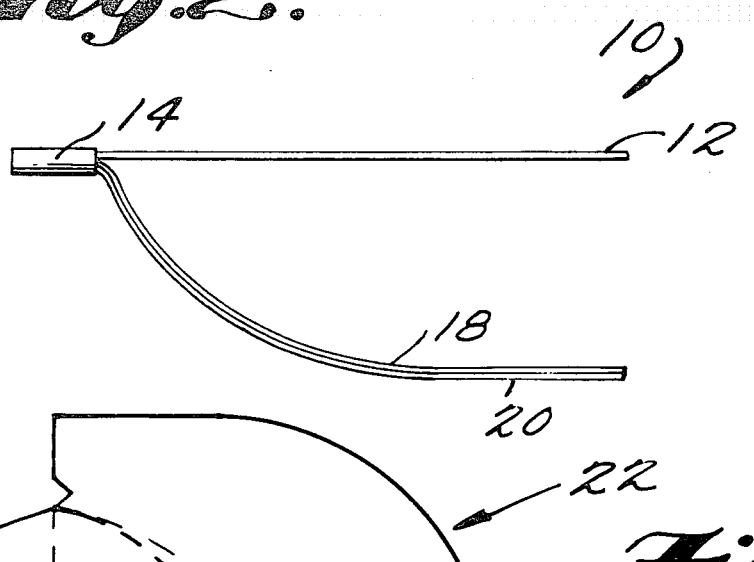
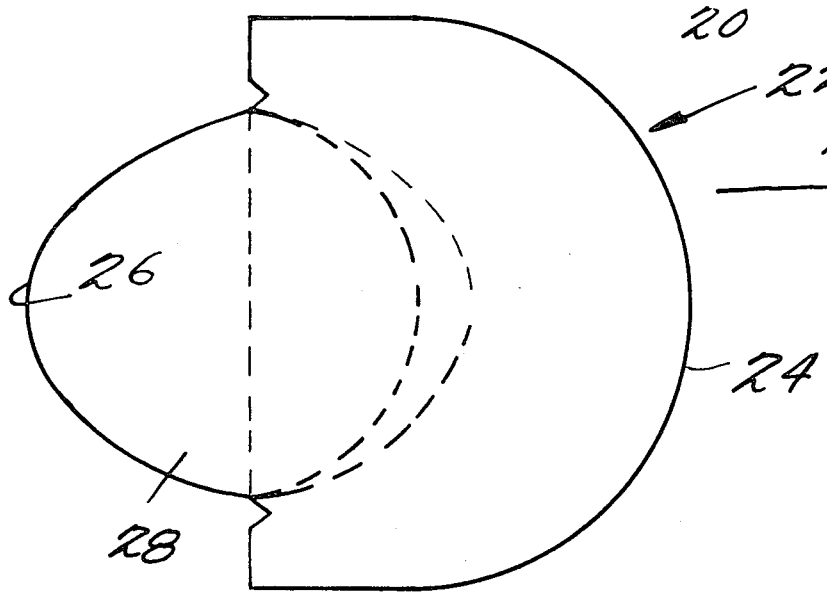

THROAT GUARD APPARATUS

BACKGROUND AND SUMMARY OF THE INVENTION

The present invention relates (1) to a throat guard, (2) to a frame for maintaining the throat guard in the desired position in a patient's mouth during a dental procedure, and (3) to the assembled combination of the throat guard and frame device.

In a number of dental procedures, the danger of small articles (e.g. dental tools, teeth, dental appliances or pieces of any of these) slipping into the patient's throat has long been known. A number of published articles reveal this to be a real existing problem with potentially life endangering aspects (e.g. when the object falls into bronchial passages). Corrective surgery to retrieve the object is often required when such accidents occur. And, in any event, the potential malpractice problems created for the doctor involved in such an accident and the mental trauma suffered by the patient under these circumstances are also very real.

In view of these obvious dangers, a number of prior devices have been proposed for preventing passage of small articles into the throat of the dental patient. One type of device that has generally been so considered and employed is a socalled "rubber dam" that is placed over and/or within the mouth of the patient and which is provided with limited openings providing access to a portion of the mouth or jaw in which work is to be done. However, such rubber dams are typically not used in everyday practice because they are difficult and time consuming to apply as well as restrictive to use. It can also give the patient a sense of lost breathing ability if the nasal air passages are or become blocked or restricted for some reason. These and other prior devices have often interfered with the dental surgeon's access to the tooth or to the portion of the jaw needing attention and/or have been uncomfortable for the patients if in place for an extended time.

Some of these prior art devices are depicted, for example, in:

U.S. Pat. No. 590,460—Mehlig
U.S. Pat. No. 1,401,646—Ronn
U.S. Pat. No. 3,406,452—McConville
U.S. Pat. No. 3,772,790—Swan-Gett et al.
U.S. Pat. No. 3,662,466—McConville
U.S. Pat. No. 4,259,067—Nelson Although Swan-Gett et al. teach a form of rubber dam which includes a bi-valve spring biased structure, they do not in any way suggest an opened spring structure capable of receiving and retaining a disposable strainer element.

Nelson teaches a relatively porous and flexible shield material. It is said to be permeable to saliva and it might presumably therefore also be permeable to air. However, Nelson arranges his shield in a vertical orientation and his bi-valve frame member does not actually extend on the outside of the teeth and jaw but, rather, is disposed inside of the teeth and jaw structure.

The remainder of the above-cited references appear of even less interest although they do appear to be generally relevant to show other prior art approaches to this same problem.

By way of contrast, I have now discovered a novel throat guard and a retention frame therefor which, separately and in combination, offer a substantial improvement over such prior devices. This novel arrangement is simple to use, requires no doctor time (it can be inserted by an assistant), has a high margin of safety, and allows total exposure for operating on all teeth in either arch of the mouth. It can also be constructed so as to be comfortably accommodated by a patient and so as not to substantially interfere with patient breathing through the mouth.

In a presently preferred exemplary embodiment, the throat guard of the present invention includes an air permeable flexible sheet material which is tear resistant when wet and which is shaped to completely occlude the throat passages from the passage of small objects. It includes a rear leaf portion which is folded upwardly and forwardly so as to seal to the hard plate of the mouth by a salivary seal. It is oversized elsewhere so as to extend at its forward and forward side edges over the patient's lower teeth and tongue with the excess resting in the lower muco-buccal fold. A desired section is cut away to provide access to any desired portion of the lower arch. The entire upper arch is automatically unobstructed at all times.

This invention also includes an exemplary embodiment for the separate retaining device which holds the throat guard in place. In the present exemplary embodiment, the retaining device includes a three-element frame which may be made of orthodontic spring wire, with each of the wires shaped so as to comfortably fit between the teeth and cheeks of the patient. Two of the wires form the lower retaining element for the throat guard, while the upper single wire element (which is biased away from the lower two elements) assists in maintaining the lower two elements in place in the patient's mouth. The upper wire element may be made of relatively heavier gauge wire to aid the retention as well as anchorage and mouth forming functions of the frame.

The combination of such a throat guard and retaining frame itself provides a novel and advantageous overall structure in which the component parts cooperate as above suggested to provide an optimum throat protection.

Stated somewhat differently, the exemplary embodiment of this invention comprises a three-element spring frame in combination with a specially shaped mouth/throat guard formed of air permeable material so as to permit breathing therethrough. Nevertheless, the mouth/throat guard provides a "strainer" structure having a mesh of sufficiently small interstices so as to catch foreign objects (e.g., dental tools, pieces of fillings, teeth, etc.) from passing on down the patient's throat. The "strainer" material is tear resistant when wet and one suitable material may be the material that breathing masks are typically made of or material such as the Telfa breathing type of bandage marketed by Colgate-Palmolive Co.

The exemplary three-element spring frame may be made of spring wire such as orthodontic wire normally used by dentists to build teeth braces or the like or it might be stamped from plastic or otherwise formed from other materials. In any event, it is generally shaped like the bi-valve jaw opening. It is dimensioned so as to fit outside the jaw and tooth structure so as to urge the cheeks away from the teeth and gums while also keeping the bottom portion of the exemplary bi-valve arrangement spring biased downwardly toward the bottom of the mouth structure. The bottom portion of the exemplary bi-valve structure actually comprises two closely adjacent elements (preferably spring biased toward one another) through which a disposable strainer element may be inserted. The strainer element is generally shaped to conform to the interior of the mouth surfaces but it includes a generally rounded posterior flap which obstructs the very back part of the throat area behind the teeth so that foreign objects are not permitted to fall down into the throat. Since this material is air permeable, the patient can easily breath through it, if required, thus not evoking a gag reflex. The posterior flap may have a fold pre-formed in it so as to project upwardly and forwardly in the back throat area.

The foregoing and other objects and advantages of my invention will become apparent as consideration is given to the following detailed description of a presently preferred exemplary embodiment taken in conjunction with the accompanying drawings, in which:

BRIEF DESCRIPTION OF THE DRAWINGS

FIG. 1 is a perspective view of an exemplary retaining device of the present invention;

FIG. 2 is a side view in elevation of the device of FIG. 1;

FIG. 3 is a top plan view of an exemplary throat guard of the present invention;

DETAILED DESCRIPTION OF THE INVENTION

Figure 4:
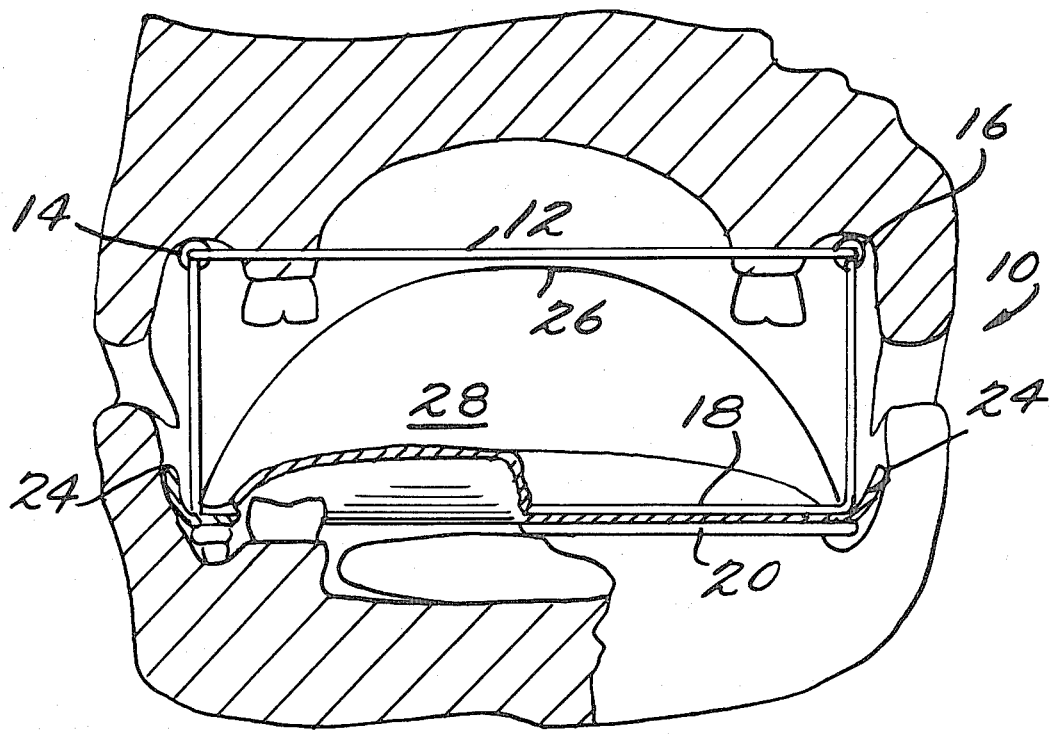
FIG. 4 is a perspective view similar to that of FIG. 1 but with the exemplary throat guard engaged in the exemplary retaining device so as to depict the combination of these two devices in accordance with the present invention.

As shown in FIG. 1, the retaining device of the presently preferred exemplary embodiment includes three generally U-shaped curved wire elements 12, 18 and 20. In practice, the device 10 can be made in several different sizes to accommodate differently sized mouth cavities of patients. While, in the illustrated embodiment, the elements 12, 18 and 20 are constructed from wire such as orthodontic wire which is resilient, other resilient structures may be employed as will be understood as this description proceeds.

The upper U-shaped wire 12 may be of a heavier gauge than wires 18, 20 so as to aid in retaining the frame within the mouth and thus securely anchoring it while also assisting in forming the outer mouth tissues away from the teeth. The upper wire 12 has its free ends securely held in anchoring members 14 and 16 which may be of metal or any suitable plastic such as polypropylene or a plastic that can withstand autoclave sterilization. Element 12 may be pressed downwardly toward the other two elements 18 and 20 to facilitate insertion into the mouth. Due to the intended spring bias between the upper wire 12 and lower wires 18, 20, the whole device then comfortably positions itself in the vestibule of the mouth between the outer segment of the teeth and the cheeks. That is, the upper wire 12 is spring biased towards an open-jaw position with respect to lower wires 18, 20. The elements 18 and 20 accordingly also have their opposite ends retained in anchoring elements 14 and 16 as shown in FIG. 1. The wires 18, 20 are, in turn, spring biased against each other by their relative shapes and common end anchoring in elements 14, 16.

In FIG. 3, there is illustrated an exemplary throat guard 22 which is made of flexible sheet material which is air permeable and which is resistant to tearing even when wet. One such type of material is sold under the trademark "Telfa" which is a breathing type bandage marketed by Colgate-Palmolive Co. The throat guard 22 has an oversized front portion 24 which is of a size sufficient to overlie at least the tongue and teeth of the lower jaw. The rear portion of the guard 22 is provided with a foldable leaf 26 which may have an accurate perimeter and which is foldable so as to totally obstruct the passage of small articles from the mouth cavity into the throat of the patient.

A natural salivary seal is formed at the boundary between the periphery of this rear leaf portion and the hard palate of the mouth. As should be appreciated, the throat guard material should have sufficient stiffness (either naturally or as induced by addition of conventional structural stiffners) to remain in an upright forwardly extending occluding position when in position and sealed to the hard palate. At the same time, it should not be so stiff as to cause discomfort to the patient or difficulty during insertion. The approximate stiffness of typically used writing paper is presently preferred.

As illustrated in FIG. 4, the outer periphery of the front oversized portion 24 of the guard 22 is engaged between wire arms 18 and 20 (which are preferably spring biased toward each other) and thus frictionally held in place. The leaf portion 26, prior to insertion into the device 10, may be folded up along line 28 to the approximate position illustrated in FIGS. 4 and 5 so as to facilitate insertion and effectuation of a salivary seal to the hard palate.

Figure 5:
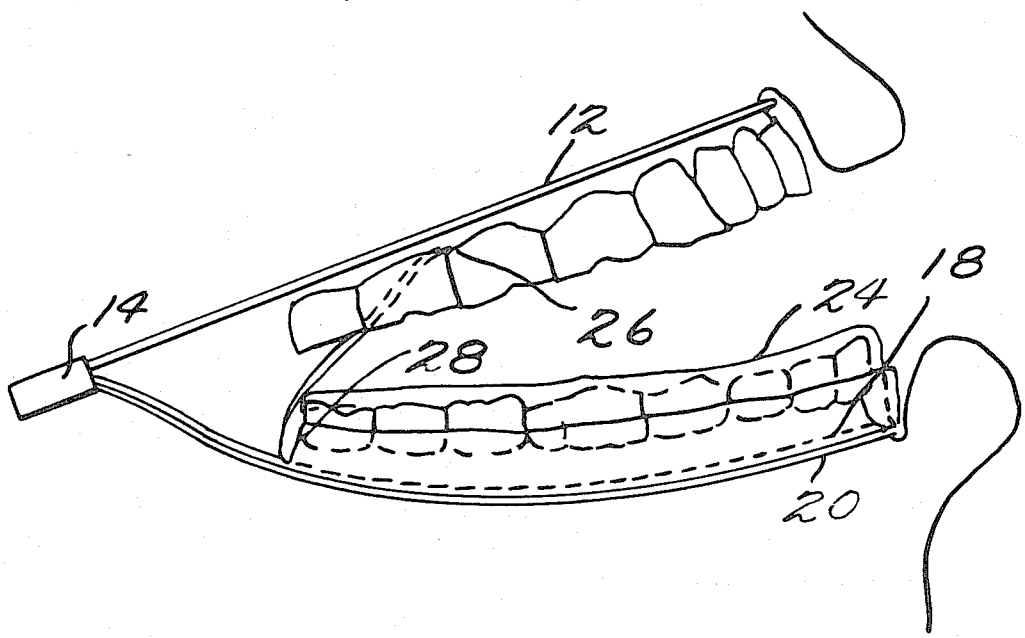
FIG. 5 is a view in side elevation showing the positioning of the retaining device and throat guard in a patient's mouth with a portion of the anatomy broken away to more specifically illustrate one possible position of the device.

As shown in FIG. 5, the upper element 12 fits around the outer periphery of the teeth of the upper jaw, and between the cheeks and upper lip while the elements 18 and 20 fit outside of the teeth and between the cheek of the lower jaw and lower lip. When in place, the outer periphery of the oversized front portion 24 of the guard 22 may extend naturally between wire elements 18, 20 over the lower arch while the leaf portion 26 will close off all (or at least the major portion) of the passage from the mouth cavity to the throat of the patient. The outer periphery of the throat guard preferably extends some three-quarters of an inch or so beyond retainer elements 18, 20 for enhanced retention ability capable of providing for the swallowing reflex of the patient. And the rear leaf portion is folded forwardly as shown to avoid endangering the airway of a gasping patient.

As earlier noted, elements 18 and 20 are preferably spring biased toward each other during construction of the device 10 so as to securely hold the periphery of the oversized forward portion of the throat guard 22 in place. Further, with the rear leaf of the throat guard disposed as illustrated in FIG. 5, the patient will typically not be subjected to the gagging reflex because (1) the rear leaf is sufficiently bent forward and (2) the major surfaces of the throat guard 22 are formed of air permeable material. Nevertheless, the leaf 26 is of a sufficient size to prevent passage of small articles such as small endodontic instruments, portions of restorations, fillings or portions of toothed material that may be dislodged or dropped during a dental procedure.

Having described one presently preferred exemplary embodiment of my invention, it will be apparent to those skilled in this art that various modifications may be made thereto without departing from many of the novel and advantageous features of the invention as defined in the appended claims.

What is claimed is:

1. A throat guard apparatus intended for insertion into the mouth of a patient so as to assist in preventing small objects from passing into the patient's throat, said apparatus comprising:

a throat guard of two dimensional flexible sheet material having a forward oversized portion of a size to overlie and project beyond the tongue and teeth of the patient's lower jaw arch and a rear leaf portion foldable upwardly and forwardly for obstructing the passage from the mouth to the throat of a patient, said rear portion being integrally connected to said forward portion and being shaped to fold upwardly so as to meet a patient's upper hard palate, and a retaining device comprising:
 a. first means for releasably retaining the oversized portion of said sheet material in a generally horizontal plane covering the patient's lower arch and the rear throat area wherein a rear-most portion of said first means is generally curved upwardly to the rear towards an anchoring position and does not retain said throat guard material,
 b. second means for resiliently engaging an upper portion of the mouth while being resiliently connected at a rear-most portion with the rear-most portion of said first means so as to offer spring bias and assist in maintaining said first means in place in the mouth cavity but not to retain said sheet material,
 c. anchoring means resiliently connecting the rear-most portions of said first and second means and adapted to reside at said anchoring position between the upper gums and cheek in rear of the mouth,
 d. wherein said first means comprises two generally U-shaped resilient elements adapted to reside between lower gums and inner lower cheek having their respective opposite ends resiliently biased towards each other and secured in said anchoring means, and wherein said second means comprises a generally U-shaped resilient element adapted to reside between upper gums and inner lower cheek having opposite ends each also retained in said anchoring means and extending away from said two elements of said first means to collectively define a bi-valve retaining frame.

2. A throat guard apparatus as in claim 1 wherein said flexible sheet material is air permeable.

3. The device as claimed in claim 1 wherein said elements comprise orthodonic wire.

4. The device as claimed in claim 1 wherein said elements comprise wire and wherein said second means comprises wire of heavier gauge than either of the individual wire elements of said first means.

5. The device as claimed in claim 1 wherein said anchoring means are made of plastic material.

6. A resilient retaining frame to help retain a disposable throat guard of sheet material in place within a patient's mouth, said retaining frame comprising:
a upper generally U-shaped member,
a lower generally U-shaped member,
said upper and lower U-shaped member being resiliently joined to one another at their respective ends to form a bi-valve frame resiliently biased towards an opened bi-valve position, said U-shaped members being sized and shaped to fit in the vestibule of a patient's mouth, outside the upper and lower teeth and inside the upper and lower cheek areas respectively, and
said lower U-shaped member including means for releasably retaining said disposable throat guard of sheet material to said lower "U-shaped member and in place overlying the tongue and lower arch teeth of the patient.

7. A resilient retaining frame as in claim 6 wherein said means for retaining comprises at least one aperture resiliently biased to a closed position for gripping a portion of said throat guard when placed therein.

8. A resilient retaining frame as in claim 7 wherein said means for retaining comprises a pair of mated U-shaped members resiliently biased toward one another.

9. A resilient retaining frame as in claim 8 wherein said U-shaped members each comprise resilient orthodontic wire.

10. A resilient retaining frame as in claim 9 wherein the upper U-shaped member is formed of heavier gauge wire than the pair of lower U-shaped members.

11. A throat guard system comprising the resilient retaining frame of claim 6, 7, 8, 9 or 10 and further comprising a throat guard formed of an air permeable flexible sheet material, said throat guard including:
a forward oversized portion sized and shaped to overlie and extend beyond the tongue and teeth of the lower arch of a human patient; and
a rear leaf portion integrally connected to the rear of the oversized portion and being sized and shaped to fold upwardly and forwardly so as to form a saliva seal with the patient's upper hard palate and, when thus in place, to obstruct the patient's throat from the passage of objects thereinto.

12. A throat guard system comprising the resilient retaining frame of claim 6 and further comprising a throat guard, said throat guard comprising:
a sheet of air permeable flexible material having an oversized front portion adapted for engagement by the retaining device and a rear leaf portion foldable upwardly and forwardly for obstructing the passage between the mouth cavity and the throat of a patient.

13. A disposable throat guard system comprising the retaining device as a claim 6 and a throat guard formed of an air permeable flexible sheet material comprising:
a forward oversized portion sized and shaped to overlie and extend beyond the tongue and teeth of the lower arch of a human patient; and
a rear leaf portion integrally connected to the rear of the oversized portion and being sized and shaped to fold upwardly and forwardly so as to form a saliva seal with the patient's upper hard palate and, when thus in place, to obstruct the patient's throat from the passage of objects thereinto.

* * * * *